US011865268B2

(12) United States Patent
Gazit et al.

(10) Patent No.: US 11,865,268 B2
(45) Date of Patent: Jan. 9, 2024

(54) DESENSITIZATION AND REPROCESSING THERAPY

(71) Applicants: Neta Gazit, Moshav Arbel (IL); Lior Gazit, Moshav Arbel (IL); Tal Bar, Ramat Gan (IL)

(72) Inventors: Neta Gazit, Moshav Arbel (IL); Lior Gazit, Moshav Arbel (IL); Tal Bar, Ramat Gan (IL)

(*) Notice: Subject to any disclaimer, the term of this patent is extended or adjusted under 35 U.S.C. 154(b) by 1150 days.

(21) Appl. No.: 16/571,371

(22) Filed: Sep. 16, 2019

(65) Prior Publication Data

US 2020/0086077 A1 Mar. 19, 2020

Related U.S. Application Data

(60) Provisional application No. 62/731,860, filed on Sep. 15, 2018.

(51) Int. Cl.
*A61M 21/02* (2006.01)
*H04L 67/125* (2022.01)
(Continued)

(52) U.S. Cl.
CPC ............... *A61M 21/02* (2013.01); *A61H 5/00* (2013.01); *G16H 20/30* (2018.01); *G16H 40/67* (2018.01);
(Continued)

(58) Field of Classification Search
CPC .......... A61M 21/02; A61M 2021/0022; A61M 2021/0027; A61M 2021/005; A61M 2205/3553; A61M 2205/50; A61M 2205/502; A61M 2205/52; A61M 2021/0044; A61M 2205/3592; A61M 2205/505; A61M 2210/0612; A61M 21/00; A61M 2230/63; A61H 5/00; A61H 2201/5012; A61H 2201/5043; A61H 2201/5048; A61H 2205/024; G16H 20/30; G16H 40/67; G16H 20/70; G16H 80/00; H04L 65/1069; H04L 67/125; H04L 65/611; H04L 65/1083; H04L 67/146; H04L 67/141; H04N 7/147; H04N 7/15; A61F 9/00; G06V 40/18
(Continued)

(56) References Cited

U.S. PATENT DOCUMENTS

| 5,343,261 A * | 8/1994 | Wilson ..................... A61H 5/00 351/203 |
| 2002/0035995 A1* | 3/2002 | Schmidt ................ A61M 21/00 128/898 |
| 2008/0038706 A1* | 2/2008 | Dameshek ............... G09B 5/06 434/309 |

* cited by examiner

*Primary Examiner* — Mohammed A Hasan
(74) *Attorney, Agent, or Firm* — NKL Law; Jae Youn Kim

(57) ABSTRACT

A system and methods for remote Eye Movement Desensitization and Reprocessing (EMDR) therapy include performing, at therapist and client computing platforms, steps of: receiving an EMDR message indicating a position a bilateral simulation (BLS) element, wherein the BLS element is at least one of a visual, an audio, and a tactile element, and wherein the indicated position is a screen position of a visual element, or a right or left position of an audio or tactile element; and responsively presenting, on the respective computing platform the BLS element at the indicated position; and performing on the EMDR server steps of: establishing connections with the therapist and client computing platforms; and broadcasting simultaneously, over the first and second connections to both the therapist and client computing platforms, the EMDR message.

20 Claims, 8 Drawing Sheets

(51) Int. Cl.
*H04L 65/1069* (2022.01)
*G16H 40/67* (2018.01)
*G16H 20/30* (2018.01)
*A61H 5/00* (2006.01)
*H04N 7/14* (2006.01)
*A61M 21/00* (2006.01)
*A61F 9/00* (2006.01)

(52) U.S. Cl.
CPC ........ *H04L 65/1069* (2013.01); *H04L 67/125* (2013.01); *H04N 7/147* (2013.01); *A61F 9/00* (2013.01); *A61H 2201/5012* (2013.01); *A61H 2201/5043* (2013.01); *A61H 2201/5048* (2013.01); *A61M 2021/005* (2013.01); *A61M 2021/0022* (2013.01); *A61M 2021/0027* (2013.01); *A61M 2205/3553* (2013.01); *A61M 2205/50* (2013.01); *A61M 2205/502* (2013.01); *A61M 2205/52* (2013.01)

(58) Field of Classification Search
USPC ........................................................ 351/203
See application file for complete search history.

DESENSITIZATION AND REPROCESSING THERAPY

RELATED APPLICATIONS

This application claims the benefit of U.S. Provisional Patent No. 62/731,860, filed Sep. 15, 2018, the entire contents of which are hereby incorporated by reference.

FIELD OF THE INVENTION

The present invention relates to the field of psychological treatment and in particular to devices for trauma therapy.

BACKGROUND

Eye Movement Desensitization and Reprocessing (EMDR) is a method of psychological therapy for the treatment of a range of psychological disorders and mental health problems, such as Posttraumatic Stress Disorder (PTSD), trauma, anxiety, chronic pain, and somatic symptoms. During EMDR therapy, a therapist helps a client (i.e., patient) to process distressing experiences. During the therapy, the client recalls experiences and representative images. The therapist guides the client through a series of bilateral stimulations (BLSs), involving side-to-side sensory stimulation, such as a light moving back and forth across a screen that the client sees, a sound switching between speakers on either side of the client, or a vibration switching between vibrating devices held in either hand of the client. The client responds to the sensory input by following the light with his eyes or by hand tapping. EMDR therapy can be viewed as including eight phases, as follows:

Phase 1 includes history taking, during which the client presents his problems and clinically significant life events are identified. Fulfilling future goals are set.

Phase 2 involves preparing the client for memory processing, as well as teaching self-control techniques. Preparation activities prepare the client to feel in control during memory processing. This phase involves "safe place" techniques, during which the client is asked to imagine a safe place, while he is engaged in a bilateral stimulation (BLS), such as visual stimulation (stimulating eye movement by a visual element moving across a screen) and\or auditory stimulation (i.e., playing of tones that alternate between left and right speakers or headphones) and\or tactile stimulation (e.g., emitting vibrations felt by the client, alternating the vibrations between tactile pulsers at either side of the client).

Phase 3 is an assessment phase. During the assessment, a memory and its different components are identified, including the symptoms that have been caused by the memory and related aspects, including an associated image, negative thoughts associated with the memory, where it is located in the body, descriptions of related emotions, etc.

Phase 4 is the desensitization process, which involves stimulating the information processing system of the client's brain, allowing insights and new connections to be made. In this phase, the client is directed to attend briefly to the identified aspects of the memory while the information processing system is simultaneously stimulated. During this phase, the client engages in periodic sets of bilateral stimulation for approximately 30 seconds each. "Stuck memory" is transformed into a learning experience and an adaptive resolution is observed.

Phase 5 involves installing new adaptive information by having the client concentrate on a desired positive belief, with periodic sets of bilateral stimulation.

Phase 6 involves having the client scan to see if there's any disturbance in the body. If there is, the memory is processed, evaluated, reevaluated, reassessed, until all of the issues have been addressed and the client is feeling empowered.

Phase 7 is the closure phase, bringing a client back to a full state of equilibrium. Phase 8 is a reevaluation phase, typically done at the next session, when the client is asked to bring back the memory and see how it feels. BLS may be performed during this phase, as well.

In 2013, EMDR was recommended by the World Health Organization for posttraumatic stress disorder (PTSD) for adults and children. As described by Solomon and Shapiro ("EMDR and the adaptive information processing model potential mechanisms of change," *Journal of EMDR practice and Research*, 2(4), 315-325, 2008), the teachings of which are hereby incorporated by reference, EMDR is based on the Adaptive Information Processing (AIP) model, which views much of psychopathology as due to maladaptive encoding of and/or incomplete processing of traumatic or disturbing adverse life experiences. The maladaptive encoding prevents integration of these memories into other memory networks that hold adaptive information. Therefore, the original perceptions are triggered by a variety of internal and external stimulations. EMDR protocols and procedures are designed to reprocess these memories. This leads to integration of the memories into adaptive memory networks, which leads to a resolution of symptoms, including an improvement in functioning, inner experience, and learning.

Online psychotherapy is a growing trend. About 20% of psychotherapists provide remote treatment by e-mail, telephone, or online communication. However, due to the interactive activities involved in EMDR therapy, when the therapist and the client are not in the same space, the therapist has difficulty overseeing the client's compliance with the BLS activities. When the therapist and the patient are not present on the same space but instead are communicating with each other via online video chat, the therapists ability to control and monitor stimulations is problematic and insufficient. One option is for the therapist to place a visual BLS generator tool in front of the web camera for a patient to view through the video chat. This option is cumbersome and does not provide a solution for the auditory and sensory stimulations. Another option is to use an online EMDR tool or EMDR computer software that runs on the patient's computer. However, this option limits the therapist's control over the stimulus. A third option is for the therapist to run an EMDR tool or software package, and to share his computer screen with his client (i.e., patient), so that the client can see the visual stimulation. Nevertheless, this option has proven to be problematic in terms of performance: when using the screen sharing function, the movement of the visual BLS element may be "jumpy" rather than continuous. Moreover, the visual stimulation on the patient computer may not appear synchronized with the therapist computer, which makes it difficult for the therapist to track the patient's eye movements to make sure the activity is done correctly. In addition, this option also does not offer a solution for the auditory and sensory stimulations. A system for improving the interactive experience could make remote EMDR more effective.

SUMMARY

An aim of the present invention is to provide a system and methods for remote Eye Movement Desensitization and Reprocessing (EMDR) therapy. In embodiments of the present invention, a system is provided including:

1) a therapist computing platform, including a therapist computer screen, a processor and associated memory storing instructions. When the instructions are executed by the processor, the processor performs steps of establishing a first connection with an EMDR server; communicating, to the EMDR server, parameters controlling a bilateral stimulation (BLS), the parameters including at least one of a start and a duration of the bilateral stimulation; receiving from the EMDR server, by the first connection, an EMDR message indicating a BLS element position, a BLS element position being a screen position of a visual element, or a right or left position of an audio or tactile element; and responsively presenting, on an output device of the therapist computing platform, at least one BLS element at the indicated position;

2) a client computing platform, comprising a client computer screen, a processor and associated memory storing instructions. When the instructions are executed by the processor, the processor performs steps of: establishing a second connection with the EMDR server; receiving from the EMDR server, by the second connection, the EMDR message indicating the BLS element position; and responsively presenting, on an output device of the client computing platform, at least one BLS element at the indicated position; and 3) the EMDR server, comprising a processor and associated memory storing instructions. When the instructions are executed by the processor, the processor performs steps of: establishing the first and second connections with the respective therapist and client computing platforms; receiving, from the therapist computing platform, the parameters controlling the bilateral stimulation; and broadcasting the EMDR message, simultaneously over the first and second connections, to the respective therapist and client computing platforms, according to the parameters controlling the bilateral stimulation.

The therapist computing platform may be configured to present a dashboard on the therapist computer screen for entering the parameters controlling the bilateral stimulation. The dashboard may include options for entering client identifying information. The dashboard may also include options for saving client preferences including the parameters for controlling the bilateral stimulation. The dashboard may also include options for entering notes regarding a session. The notes may reflect one or more of: a target; an image; positive cognition; negative cognition; Subjective Units of Disturbance (SUD), Validity of Cognition (VOC); client emotions; client body sensations; final SUD; and other remarks.

Parameters controlling the bilateral stimulation may include a speed of altering a position of the at least one BLS element. The parameters may also include at least one of a set of visual element features including: color, opacity, size, shape, brightness, a movement mode, a height, a direction path, a tracking path, path end points, and a background color. The movement mode may include a scanning mode and a saccades mode. The parameters may also include at least one of a set of audio element features including volume, a sound effect, and music. The parameters may further include a tactile element feature of a vibration intensity of the tactile element. The EMDR server may broadcasting simultaneously, over the first and second connections to the respective therapist and client computing platforms, a second EMDR message including at least one parameter of the set of the visual element features, of the audio element features, and of the tactile element feature.

In some embodiments, the therapist and client computing platforms include establishing a video chat session with the other computing platform. The video chat session may be a WebRTC video chat, and the EMDR server may be configured to provide signaling to establish the WebRTC video chat.

The therapist computing platform may be configured to display a level of correspondence between the client eye movement and the movement of the visual element on the client screen. An image processing algorithm may execute on the client or therapist computers to identify eye motion of the client and to correlate that eye motion with eye movement of the BLS visual element to generate the level of correspondence.

The EMDR server may be further configured to automatically modify at least one parameter controlling the BLS according to a level of correspondence between the client eye movement and the movement of the visual element on the client screen.

The instructions executed by the therapist computing platform and the client computing platform may include client-side applications received from the EMDR server by a browser of the respective computing platforms.

The first and second connections between the EMDR server and the respective therapist and client computing platforms may be Socket.IO connections.

In some embodiments, the EMDR message indicating a position of a BLS element indicates a position of two or more of the visual, audio, and tactile elements, such that the positions of the multiple BLS elements are synchronized to be on the same side, to the left or right side of the client.

The position of the BLS element on the client computer screen may be presented at a mirrored position of the position of the BLS element presented on the therapist computing platform.

At least one of the therapist and the client computing platforms may be configured to provide an indicator on the screen of the respective computing platform that on at least one of the first and second connections with the EMDR server has been established.

There is also provided, by embodiments of the present computer, a computer-based method for remote Eye Movement Desensitization and Reprocessing (EMDR) therapy, the method including:

1) at a therapist computing platform that has a processor and associated memory including instructions for implementing steps of the method, establishing a first connection with an EMDR server; communicating, to the EMDR server, parameters controlling a bilateral stimulation (BLS), wherein the parameters include at least one of a start and a duration of the bilateral stimulation; receiving from the EMDR server, by the first connection, an EMDR message indicating a position of at least one BLS element, wherein the at least one BLS element is at least one of a visual, an audio, and a tactile element, and wherein the indicated position is a screen position of a visual element, or a right or left position of an audio or tactile element; and responsively presenting, on an output device of the therapist computing platform, the at least one BLS element at the indicated position;

2) at a client computing platform that has a processor and associated memory including instructions for implementing steps of the method, establishing a second connection with the EMDR server; receiving from the EMDR server, by the second connection, the EMDR message indicating the position of the at least one BLS element; and responsively presenting, on an output device of the client computing platform, the at least one BLS element at the indicated position; and at the EMDR server that has a processor and associated memory including instructions for implementing steps of the method, establishing the first and second connections with the respective therapist and client computing platforms; receiving, from the therapist computing platform, the parameters controlling the bilateral stimulation; and broadcasting the EMDR message, simultaneously over the first and second connections, to the respective therapist and client computing platforms, according to the parameters controlling the bilateral stimulation.

BRIEF DESCRIPTION OF DRAWINGS

Embodiments of the invention are illustrated by way of example and are not limited to the figures of the accompanying drawings, in which like reference numerals indicate corresponding, analogous or similar elements, and in which.

Figure 1:
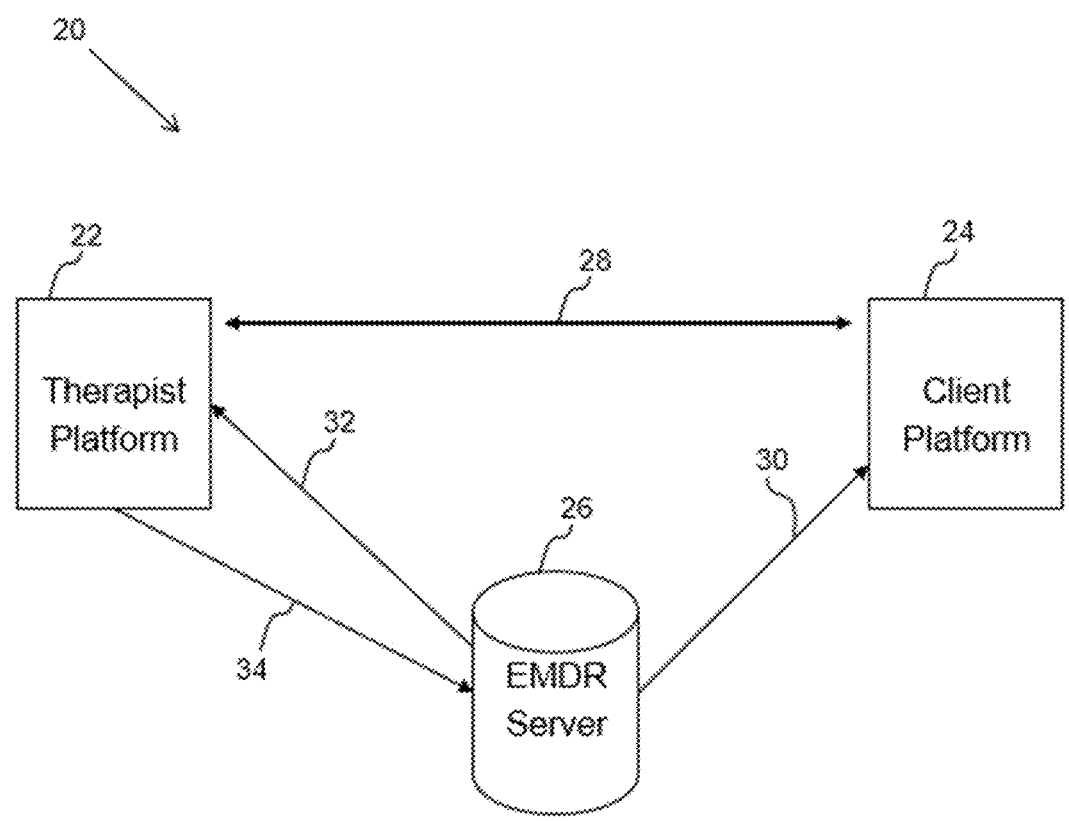
FIG. 1 is a block diagram, depicting a system for remote EMDR, in accordance with an embodiment of the present invention.

Structural details of the invention are shown to provide a fundamental understanding of the invention, the description, taken with the drawings, making apparent to those skilled in the art how the several forms of the invention may be embodied in practice. Reference numerals may be repeated among the figures to indicate corresponding or analogous elements.

DETAILED DESCRIPTION

In the following detailed description, specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

FIG. 1 is a block diagram, depicting a system 20 for remote EMDR, in accordance with an embodiment of the present invention. System 20 is designed to provide an administering user (i.e., a therapist) with the ability to remotely control and monitor EMDR activities (i.e., bilateral stimulations) presented to the client. System 20 may also facilitate a video chat between the client and the therapist. The EMDR activities include stimulations by audio, visual, and tactile elements, collectively referred to hereinbelow as "BLS elements."

System 20 includes a therapist platform 22, a client platform 24, and an EMDR server 26. The therapist platform, the client platform, and the EMDR server are computing platforms that typically includes one or more processors (i.e., CPUs), typically provided as computing chips or as any suitable computing device, and including memory and a storage system, which typically stores an operating system and executable code. The processors may be configured to carry out methods described herein, and/or to execute or act as the various modules, units, etc. More than one processor may perform each task, and one or more processors may operate in a distributed manner to implement all the indicated functions. Operating systems of the various devices may include code segments configured to perform tasks involving coordination, scheduling, arbitration, supervising, and controlling of the computing devices, for example, scheduling execution of software programs or enabling software programs or other modules or units to communicate. Executable code may be executed by processors possibly under control of the operating system. In some embodiments, some of the components described may be omitted. For example, the memory may be a non-volatile memory having the storage capacity of a storage system, such that the storage systems may be embedded or included in the memory.

The computing platforms typically also include input devices and output devices. Input devices of the platforms may include a mouse, a keyboard, a touch screen or pad or any suitable input, as well as a microphone and a camera to enable two-way video conferences. Output devices may include one or more displays or screens, speakers, headphones, and tactile output devices, such as tactile pulsers. The computing platforms also include wired or wireless network interface cards to facilitate remote communications.

In embodiments of the present invention, the therapist platform 22 and the client platform 24 may be desktop computers having typical operating systems such as Microsoft Windows. Alternatively, the therapist and client platforms may be any type of interactive computing devices, such as mobile devices. Both platforms also typically include an internet browser, such as Google Chrome, as the means of interfacing both with the EMDR server 26 and with each other.

The EMDR server may similarly be any type of computing device including remote networking capabilities. In some embodiments, the EMDR server may be a cloud-hosted server that operates, for example, on a cloud service such as Amazon Web Services Elastic Computing Cloud. The EMDR server 26 typically runs a web server, such as a web server based on Node.js, and may be built with support of the following technologies:

MongoDB—cross-platform document-oriented database program.

Socket.IO—a JavaScript library for web applications, enabling real-time, bi-directional communication between web clients and servers.

Angular—TypeScript-based open-source web application framework.

NgRx Store—reactive state management for Angular apps.

WebRTC—open-source project that provides web browsers and mobile applications with real-time audio and video communication.

In typical embodiments, applications run on the therapist and client platforms as browser-based applications, i.e., "client-side code," which is loaded to the browsers when the browsers are directed to a webpage of the EMDR web server. The application executed on the therapist platform is referred to hereinbelow as the therapist application, and the application executed on the client platform is referred to as the client application. The EMDR server may also execute an EMDR application that is configured to establish socket connections with the therapist and client applications, as described further hereinbelow. It is to be understood that the EMDR server may be a distributed system, such that functions of the system, such as the EMDR web server and the EMDR application, may operate on different physical computers.

In some embodiments, the client and therapist applications present visual, audio, and/or tactile elements during bilateral stimulations, such as presenting a light moving back and forth across the screen, or a sound or vibration alternating between two speakers or two vibrating devices. The applications may also present a video chat between the therapist and the client, through which the therapist can engage the client to implement the phases of EMDR described above, while also monitoring a client's reactions to bilateral stimulation. Although optional, the video chat, when implemented, also enables the client and the therapist to confirm with each other that a communications channel exists for a bilateral stimulation to proceed. For example, the client can confirm that the visual element appears on his screen. The video chat may be implemented as a peer-to-peer connection 28 between the browser-based web applications. The peer-to-peer connection may be implemented by WebRTC protocols or other types of peer-to-peer video communication technologies, as well as by a third party video chat software package, such as Skype.

During bilateral stimulation, visual, audio, and tactile elements are presented on the client platform 24. Visual elements are typically displayed on the client platform screen. Audio elements are output from the client platform speakers (typically placed on either side of the client) or headphones, and may include music or sounds, which alternate between the speakers. Tactile elements are output from devices that are meant to be touched by the client, such as a "tactile pulsers" that emit pulses of vibrations and which may be touched or held by the client (for example, strapped to each hand). The vibration pulses also alternate back-and-forth between the pulse devices. The tactile pulsers may be connected by USB or by Bluetooth to the client platform.

The client and therapist applications present the visual, audio, and tactile elements at positions, and with features, that may be determined by EMDR messages delivered (i.e., "pushed") synchronously to the client and therapist applications from the EMDR application over respective communications links 30 and 32. The communications links 30 and 32 may both be, for example, web socket sessions. The communications links 30 and 32 may be socket sessions with a single "room" implemented by the EMDR application, using, for example, based on the Socket.IO JavaScript library, which enables the EMDR application to send practically simultaneous messages to both sessions with a single command.

In some embodiments, the EMDR application may be configured to simultaneously stream, to both the client and therapist applications, EMDR position messages that include a position of a BLS element. The rate at which the EMDR position message is sent may be determined by an EMDR speed parameter, as described below. The client and therapist applications may be configured to react immediately to new EMDR messages, to display the visual element at the new position or to emit the sound and/or vibration on the side of the client as defined by the received message. In some embodiments, a value of a position variable in the position message is set to rise and to fall between limits that define the edges of the client screen. Alternatively, the visual element may be set to switch back and forth between the edges of the screen, representing a movement mode termed as "saccades." The EMDR position message in saccades mode may be set to only deliver the minimum or maximum position values. Whether the visual element is set to saccades or continuous "scan" mode, the audio and tactile elements are typically presented in saccades mode, being presented on alternating sides of the client when the position value reaches the minimum and maximum values. In further embodiments, the visual element may be set to be inactive, in which case only the audio and/or tactile elements are presented.

In some embodiments, the client and therapist applications may use an HTML "style" definition to define a visual element as an object array, where the array indices correspond to different screen positions. An EMDR message may indicate an index of the visual element, which is then translated to a screen position by each browser of the respective client and therapist applications. The EMDR message may also indicate a position that the client and therapist applications apply to all currently active BLS elements, thereby synchronizing the "movement" of the currently active BLS elements. For example, the client and therapist applications may be configured to emit sounds and/or vibrations when a position (or array index) specified by an EMDR message reaches the limit (i.e., the screen edge), thereby synchronizing the visual element position with the audio and tactile elements. A tactile element on a client's right side will then vibrate when the visual element moving across the client's screen reaches the right side, or a speaker on the right side will emit a sound. While a bilateral stimulation is being conducted on the client platform, some or all of the same BLS elements may also be presented at the therapist platform 22 in order to enable the therapist to monitor the activity.

A "dashboard" may be implemented as part of the same therapist application that presents the stimulation elements and the video chat, enabling the therapist to control parameters of bilateral stimulations. The parameters that may be controlled through the dashboard may include start and stop triggers for the BLS, a duration and a type of a bilateral stimulation, as well as any or all of the other aspects of the bilateral stimulations. The therapist typically sets these parameters to suit client preferences. Parameters are typically set before a set of bilateral stimulations begins, but they can also be changed during a stimulation activity when appropriate. That is, sometimes there is a need to change an EMDR set, that is, to change the predefined set of bilateral stimulations, according to client needs while a BLS activity is being conducted.

Some of the dashboard controls may include the following:

Start and stop controls: starting and stopping a bilateral stimulation including a visual element moving back and forth across a client's screen.

Speed control: the speed of the stimulations. Sometimes there is a need to change the speed stimulations within different parts of the therapy (for example, at the beginning, there is need for slower speed than during processing).

Color and opacity control: the visual element color and opacity. Some colors can be triggering and some relaxing for some clients.

Visual element size control: the visual element size.

Visual element shape control: the visual element shape, which may be set to any image or icon.

Visual element brightness control.

Visual element display mode control: The movement of the visual element may be set to scan, meaning containing the whole movement path from left to right and back (scanning), or to saccades, meaning jumping directly from side to size.

Visual element direction path control: left-right vs. right-left; up-down vs. down-up.

Visual element tracking path control: The shape of the track along which the visual element moves, which may be vertical, horizontal, diagonal, infinity sign, parabola, etc. The right and left end points of the visual element path may also be set. Sometimes there is a need to change the tracking path of an EMDR set, according to client needs.

Visual element height control: the visual element position while going across screen (height from bottom of screen, or level such as low, middle, high, etc.). Like other parameters, the height can also be changed by the therapist during an EMDR set, that is, while a set of bilateral stimulations are being performed, for example when client processing is stuck.

Visual element background color control: the screen background color, behind the visual element.

Auditory element sound control: tone, sound effect, or music, as well as volume.

Tactical element intensity control: intensity of vibration.

Set duration control: The duration of a set of bilateral stimulations may be predefined according to the needs of the client during therapy, for example for long or short processing, etc.

BLS type control: specifying which of the BLS elements (visual, audio, and/or tactile) are active.

Other client preferences: The therapist can save client's preferences, so that in subsequent sessions he can easily upload them. There may be several save slots for each client, so that every client could have several saved preference definitions for different parts and needs during the therapy.

When a therapist modifies a parameter of the bilateral stimulation from the dashboard, a message is sent to the EMDR application, over a communications link 34, indicating the parameter change. The communications links 32 and 34 may be the same Socket.IO session, which provides a two way communications link. It should be noted that the communications link 30 between the EMDR server and the client platform is also typically the same type of two way communications link as the link between the EMDR server and the therapist platform. After receiving a new therapist message, the EMDR application then generates an EMDR message to send to both the client and therapist applications, to ensure that changes in aspects of a bilateral simulation occur simultaneously on both the client and therapist platforms. The generation of EMDR messages is performed according to parameters set by therapist messages, in particular the start control parameter, as well as parameters for BLS speed, duration, and type.

The therapist dashboard may also include options for assisting the therapist with additional aspects of EMDR therapy. For example, the dashboard may include options for saving client preferences for BLS parameters. These parameters may be saved in a file in disk storage, or in other permanent storage on the therapist platform, or at the EMDR server. As described above, the BLS parameters may include such features as: the color of the visual element, the color of the background, the BLS speed, a set duration (i.e., the duration of a set of activities), the type of the visual element (ball, star, etc.), the sound type and pitch, etc.

The therapist dashboard may also enable the therapist to edit and to save a client profile, which covers technical information about the client, including, for example: email and other contact info, number of sessions, time and duration of the last session, as well as therapist notes on client progress. For each profile, there may be several options for saving data about a given client, data that may then be applicable to other parts of a session.

The therapist dashboard may also permit a therapist to directly enter notes about a specific client session, which typically includes several activities. These notes may include professional analysis of a session, such as: target; image; positive cognition; negative cognition; Subjective Units of Disturbance (SUD), Validity of Cognition (VOC); client emotions; client body sensations; final SUD; and other remarks.

Figure 2:
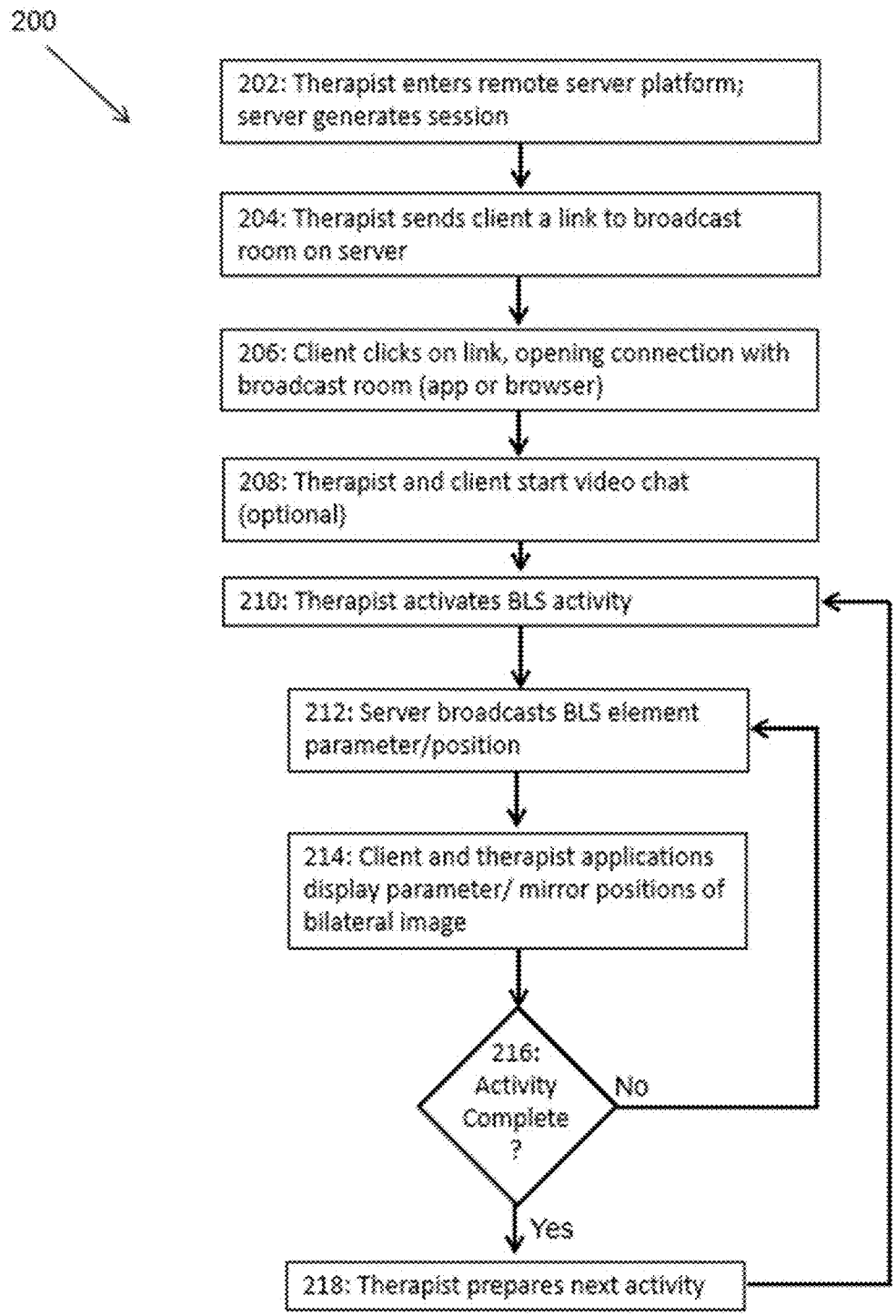
FIG. 2 is a flow diagram, depicting operation of a system for remote EMDR, in accordance with an embodiment of the present invention.

FIG. 2 is a flow diagram, depicting a process 200 for implementing remote EMDR by system 20, in accordance with an embodiment of the present invention.

At a first step 202, a therapist opens a web browser or platform-based application (such as a mobile device "app") and directs the browser to an internet URL of the EMDR server. A web server on the EMDR server, such as a Node.js server, may respond by sending client-side code to the therapist web browser or platform-based application. The client application may be similarly implemented as client-side code, in a browser on the client platform. In some embodiments, the client-side code may be code that is compiled by the Angular framework. The client-side code typically begins by presenting a sign-in page for the EMDR application.

Once the therapist has signed in (typically requiring a password or other security measures), the therapist application may present the therapist with options to start a session based on a previously entered client definition, or to create a new client definition, inputting general details such as name, email and country.

To start a session, the therapist may click on a "Start Session" option, initiating a request to open a communications connection by which the EMDR application can push messages to the therapist application. The request may include a "sessionId" that is unique for each of the therapist's clients. The EMDR application may be configured to receive the request and to create a communications session between the therapist application and the EMDR application. The session may be a WebSocket session, which may also define a Socket.IO room, where the unique session id ("sessionID") is the room name. The EMDR application may also create an instance of "EMDRSession", a process that manages the state of the session and enables relaying and broadcasting messages to "members" of the Socket.IO room, i.e., to all processes that have opened a WebSocket connection to the room.

At a step 204, in order to invite a client to the EMDR session (if the client has not previously stored the URL of the unique session), the therapist copies a link containing the unique session id, and sends it to the client via email or any other means. A typical url link may appear as follows:
https://[emdr domain name]/session/5d370dfd1?videoChat=true At the client platform, at a step 206, the client may enter the provided URL in his browser, thereby accessing the EMDR application, which may present to the client a 'Join Session' button. Clicking on the button may initiate a request to the EMDR application to create a WebSocket connection with the client application, which, for example, may be a connection to the same Socket.IO room to which the therapist web browser was connected. The EMDR application may create the connection, joining the client to the room.

Through the dashboard of the therapist application, as described above, the therapist may send commands (i.e., messages) to set the EMDR parameters, the commands being transmitted to EMDRSession, as described above. These commands include parameters that set how a visual element will appear and move, as well as aspects of audio and tactile elements, such as whether or not these elements will be used (i.e., whether on or off) and if used, what sound or tactile output will be provided. As described above, the audio and tactile elements may be synchronized with the visual output, for example ringing or vibrating each time the visual element reaches the edge of its track (for example, the edge of the screen). The commands update the state of parameters maintained by the EMDRSession. These parameters are turn broadcast by the EMDR applications to the members of the room, i.e., to the client and therapist applications.

Typically following the creation of the EMDR connections, the client and therapist applications may also initiate a video chat between each other at a step 208. The EMDR application may also serve as a signaling server when establishing a direct WebRTC peer-to-peer video chat connection between the therapist and client. As described in the MDN web docs for WebRTC, the contents of which are incorporated herein in their entirety, a signaling server provides the two processes with the necessary identifying information for establishing a connection "while minimizing exposure of potentially private information as much as possible." The MDN web docs for WebRTC are available at: https://developer.mozilla.org/en-US/docs/Web/API/WebRTC_API/Signaling_and_video_calling At a step 210, the therapist may initiate a bilateral stimulation from the dashboard of the therapist application, whereby a message is sent to the EMDRSession process to start a session based on the current parameter settings (i.e., the current session state). The start message may set the EMDRSession state to "Play," which may create socket streams from the EMDR application to the respective client and therapist applications.

At a step 212, the EMDR server begins broadcasting EMDR messages to the client and therapist applications to modify the BLS elements, in particular the BLS element position. The broadcasting of BLS element positions may be streamed over a socket at a rate determined by a speed control set by the therapist, as described above. The streaming of the EMDR messages including a BLS element position may continue for the period of time set by the duration control, as described above. The streaming of BLS element position messages has the effect of "moving" the visual element and/or playing sounds, and/or causing tactile output, depending on which BLS elements have been defined as being active. Additional EMDR messages may also be sent ad hoc to change other BLS element features, in response to changes initiated by a therapist from the dashboard.

EMDR messages are received at a step 214, typically by both the client and the therapist's applications. The applications are typically configured to process and implement received messages immediately. For example, the applications may convert such messages to NgRx Store actions, and the received parameters may be defined as "observable" parameters that immediately initiate respective updates of the web interface (when, for example, the client and therapist applications are written in Angular™ code, with the RxJS library). In effect, the messages from the server create an animation effect of moving the visual element. In some embodiments, the visual element may be defined as an HTML element, such as "LED" (typically an array). The EMDR message may indicate the position and number of the LEDs that are to appear on the screen. The broadcast EMDR messages may change the currently "active" LEDs every few hundredths of a second, depending on the current "speed" setting. At a rate set by the speed setting, the EMDR application may send new messages changing the active LEDs. The position of the active LEDs may be either incremented (for example, moved to the right) or decremented (moved to the left, or vice versa).

The streaming of broadcast messages may continue as long as, at a step 216, a preset definition of the activity, or of a set of multiple activities, as defined by the therapist, has not been completed, or as long as the therapist does not intervene to send a BLS "stop" message. That is, the EMDR application may continue to broadcast messages, and the client and therapist applications may continue to present BLS elements at new positions, according to the messages. As described below, the client application may also make several modifications to the appearance of the client screen when a bilateral stimulation is initiated. At a step 218, the bilateral stimulation ends and the streaming of messages stops. The client application may also restore the initial appearance of the application screen, as indicated below.

FIGS. 3-8 are screenshots of therapist and client screens during an EMDR activity of bilateral stimulation, in accordance with an embodiment of the present invention. It is to be understood that the screens shown may be windows, covering all or part of the monitors of the respective therapist and client platforms.

Figure 3:
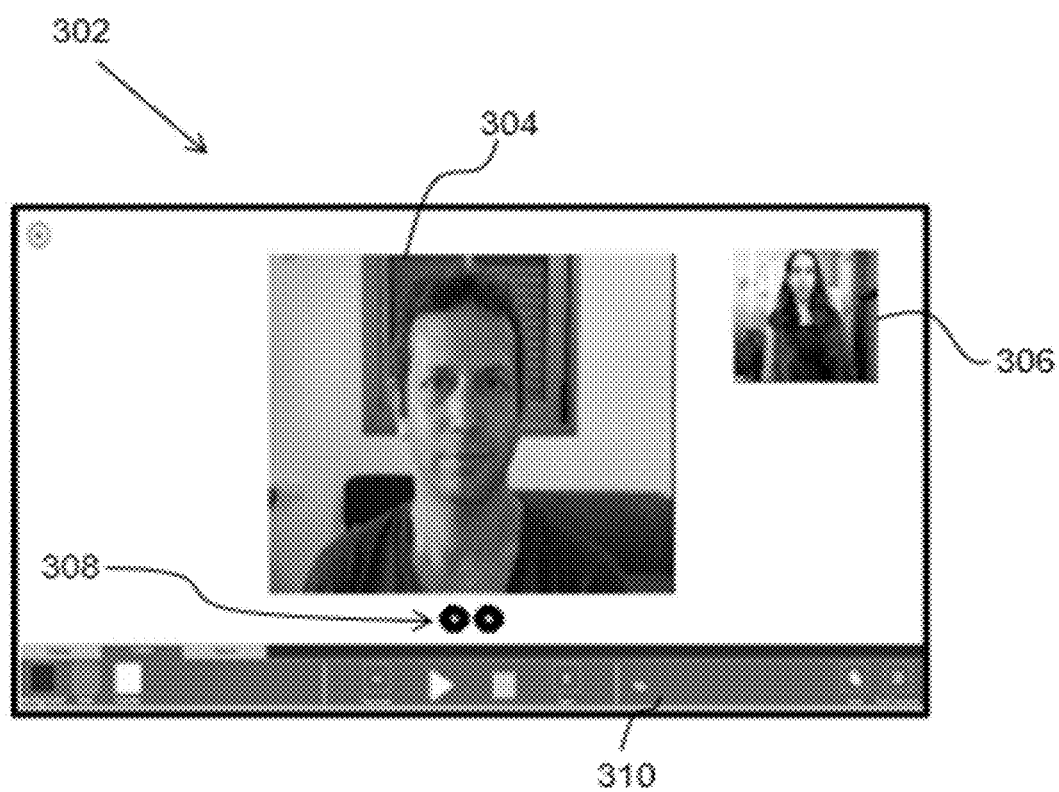
FIGS. 3-8 are screenshots of therapist and client screens during an EMDR activity of bilateral stimulation, in accordance with an embodiment of the present invention.
Figure 4:
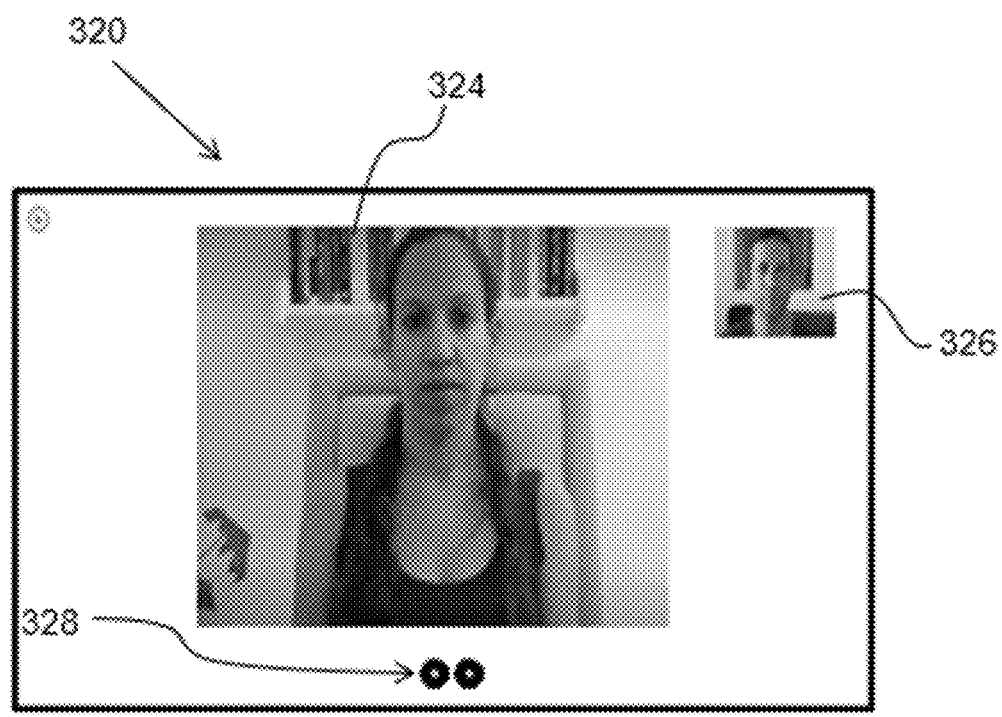

FIGS. 3 and 4 show examples of a therapist screen 302 and of a client screen 320, before a bilateral stimulation begins. The therapist screen 302 shown in FIG. 3 may include a view of a large video stream window 304 of the client, and a small video stream window 306 of the therapist. It should be noted that the video chat feature is optional and, if used, may also be provided in a separate window or on a separate display by external third party video chat applications. Also shown on the therapist screen 302 is a visual element 308 for a bilateral stimulation, while the client screen 320 shows a similar visual element 328. As shown in the figure, the visual element appears as a pair of neighboring LEDs. Alternatively, the system could be configured to display any type of image or icon. At the bottom of the therapist screen there are dashboard controls 310, which, as described above, can be used to change aspects of the visual element, such as its color, shape, and speed, while also starting or stopping the bilateral stimulation and controlling use of the audio and/or tactile output. An additional indicator that may appear on the therapist screen is an indicator that the client platform has made a data connection (such as a WebSocket connection) to the EMDR application. A similar indicator may also be configured to appear on the client screen.

The client screen 320 shown in FIG. 4 may include a view of a large video stream window 324 of the therapist, and a small video stream window 326 of the client, as well as the visual element 328. Typically the client screen does not include dashboard controls, as a BLS session typically requires that the client not have distractions.

Figure 5:
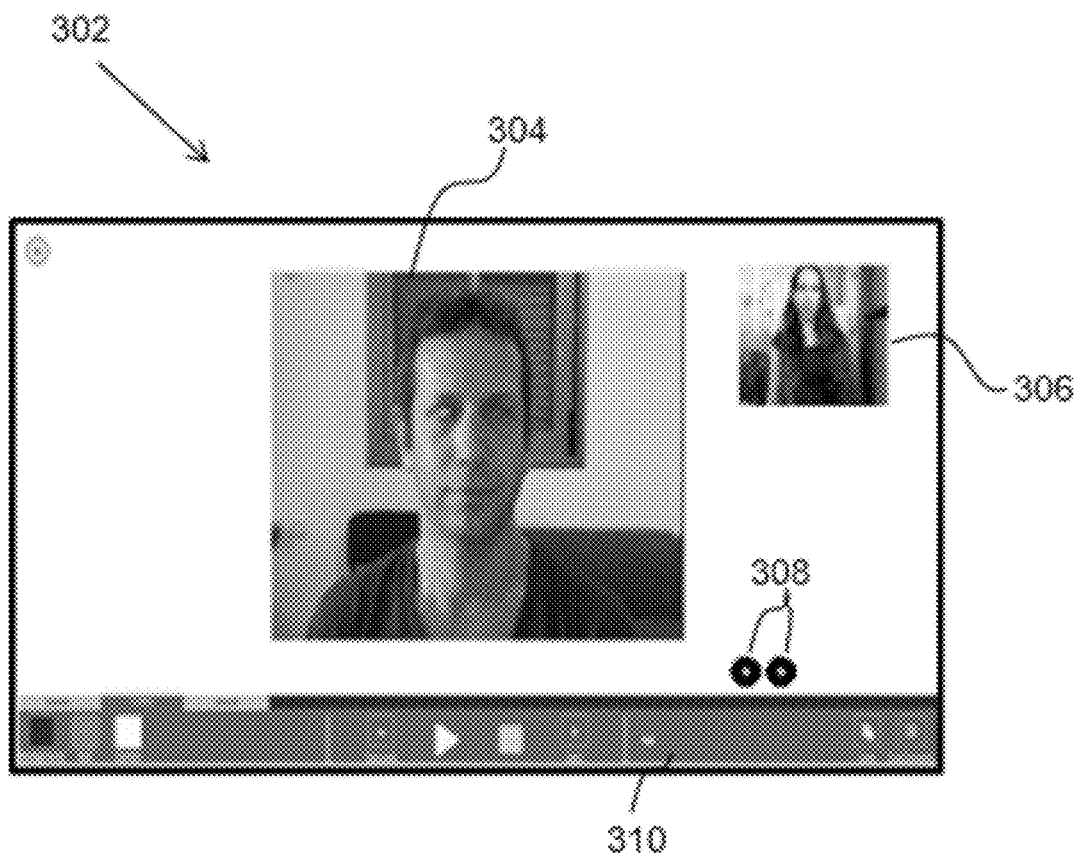
Figure 6:
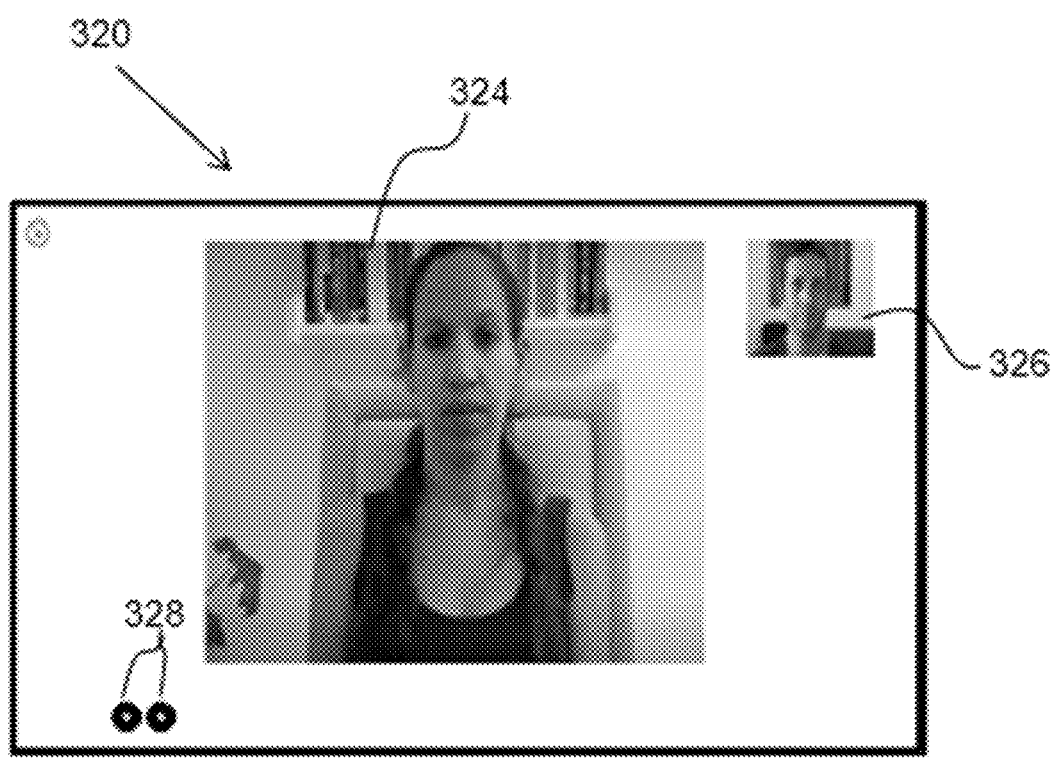

FIGS. 5 and 6 show the respective therapist and client screens, 302 and 320, after a bilateral stimulation begins. The therapist screen may continue to display the large video stream window 304 of the client, and the small video stream window 306 of the therapist. Also shown on the therapist screen 302 is a visual element 308, while the client screen 320 shows a similar visual element 328. As indicated in the figures, the client and therapist applications may be configured to provide a mirror effect of the movement of the visual element. That is, one of the applications (for example, the client application) may be configured to reverse the direction of the visual element, such that while the client application, for example, presents the visual element moving from right to left, the therapist application presents the visual element moving from left to right. Consequently, when the visual element 308 is seen towards the right of the therapist screen 302, the therapist sees the client in the video chat looking towards the visual element 308, even though the client is actually looking to his left. As seen in the client screen 320, the client is looking to his left because his screen shows the visual element 328 on the left side of the screen.

The mirroring of the movement of the visual element may be implemented on either the client or therapist browser by setting an HTML "style" of the visual element to be "RTL", that is, the reverse of the default direction. (Other visual element parameters, such as the position and height controls, may also be implemented by setting HTML style definitions to define the alternative visual aspects, and then including the selected alternative in the EMDR message.) It should be noted that the appearance of the visual element, as well as the mirroring of the movement of the visual element are both optional features. The system may also be configured so that these features may be enable or disabled by the therapist. In further embodiments, the auditory and tactile elements may also be output (i.e., emitted as sound and vibrations) on the therapist platform, as well as on the client platform, and may also be mirrored. As described above, the multiple BLS elements are typically synchronized when used together for stimulation. That is, a tactile element on a client's right side may vibrate when the visual element moving across the client's screen reaches the right side, and/or the right speaker or headphone may emit at that moment the audio tone.

Figure 7:
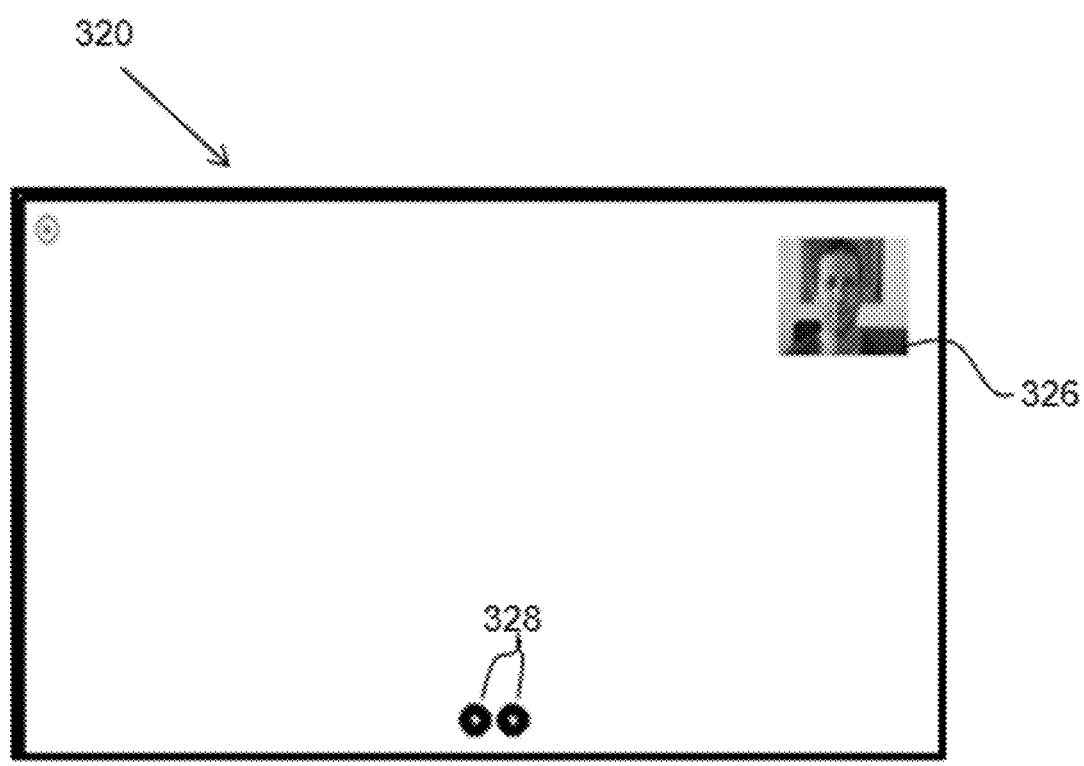
Figure 8:
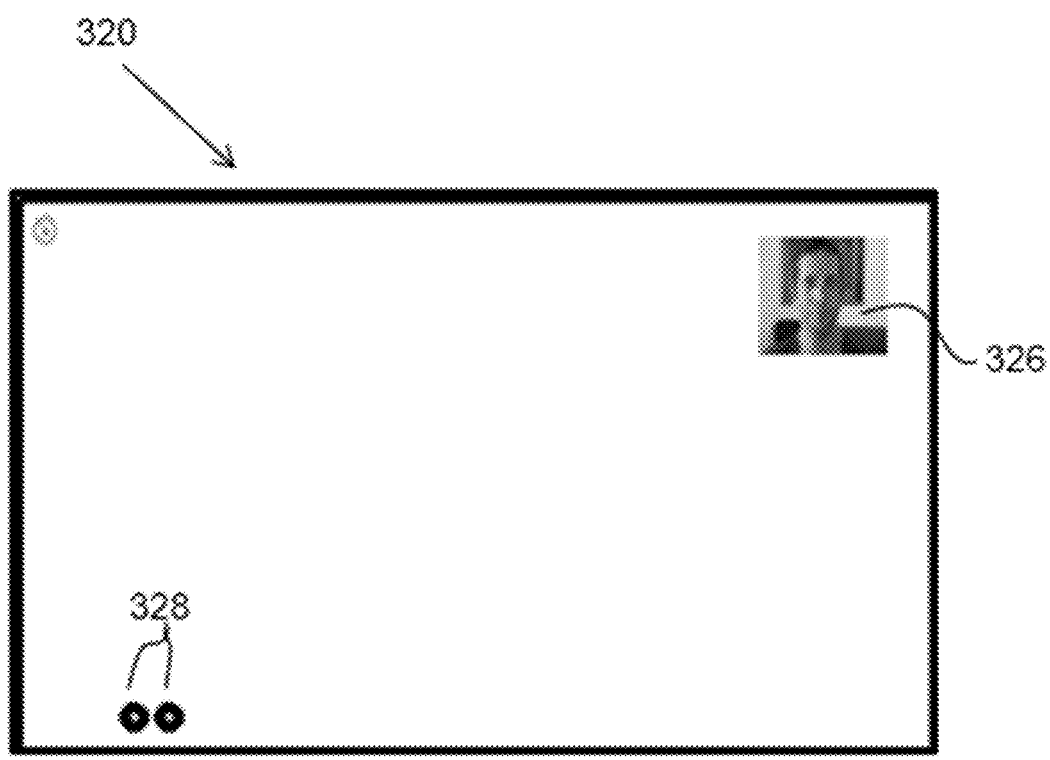

FIGS. 7 and 8 show alternative configurations of the client screen 320, after a bilateral stimulation has begun. In these views of the client screen, the large window showing the therapist video chat has been removed. The client application may remove either or both of the chat windows when a bilateral stimulation begins, in order to reduce visual distractions that could interfere with the bilateral stimulation being experienced by the client.

It should be noted that a key aspect of the client platform is that the camera of the client platform should be positioned on a center axis of the client's screen (for example, centered at the top of the screen), so that the therapist can monitor eye movement of the client while the client is following the moving visual element during the bilateral stimulation.

In a further embodiment, the therapist may initiate multiple video chats with multiple clients, while arranging for all the clients to enter the same Socket.IO session, so that all receive the same, simultaneous BLS messages. In such a scenario, multiple clients all see, hear, and sense the same elements activated at the same time, while the therapist can view all the clients reacting in multiple, respective video chat windows. The dashboard may be configured to allow the therapist to mute his communication with all except one client, so that private interactions may also be facilitated.

In a further embodiment, the client or therapist application may include performing image processing of a real time video recording of the client to identify eye movements of the client. Typically, the real time video recording is the video recording performed for the video chat between the client and the therapist. The image processing tracks the eye movement and determines a level of correspondence between the eye movement and with the movement of the visual element on the client screen. The level of correspondence can be indicated to the therapist, who can then determine if parameters of the bilateral stimulation should be changed accordingly, such as changing the speed, type, or range of movement. The EMDR server may also be configured to automatically modify the bilateral stimulation according to the level of correspondence. For example, the EMDR server may be configured to incrementally increase the speed of the visual element while the correspondence is better than 95%, and to decrease the speed when the correspondence is less than 90%.

It will be apparent to those skilled in the art that certain communications technologies described above may be replaced by other similar technologies. By way of example, a variety of web servers and web socket APIs may be used to implement the functions of the EMDR server. In addition, socket communications implemented through browser-based applications on the client and therapist platforms may be implemented through platform-based applications, including mobile device applications.

Although embodiments of the invention are not limited in this regard, discussions utilizing terms such as, for example, "processing," "computing," "calculating," "determining," "establishing", "analyzing", "checking", or the like, may refer to one or more operations or processes) of a computing platform, a computing system, or other electronic computing device, that manipulates or transforms data represented as physical (e.g., electronic) quantities within the computer's registers and/or memories into other data similarly represented as physical quantities within the computer's registers and/or memories or other information non-transitory storage medium that may store instructions to perform operations and/or processes. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Computing platforms, according to embodiments of the invention, may include one or more computing devices. Computing devices may include mobile devices. Methods according to embodiments of the invention may be carried out by one or more computing devices as described herein. Processing elements of the system described herein may be implemented in digital electronic circuitry, or in computer hardware, firmware, software, or in combinations thereof. Such elements can be implemented as a computer program product, tangibly embodied in an information carrier, such as a non-transient, machine-readable storage device, for execution by, or to control the operation of, data processing apparatus, such as a programmable processor, computer, or deployed to be executed on multiple computers at one site or one or more across multiple sites. Memory storage for software and data may include multiple one or more memory units, including one or more types of storage media. Examples of storage media include, but are not limited to, magnetic media, optical media, and integrated circuits such as read-only and random access memory devices. Network interface modules may control the sending and receiving of data packets over networks. Method steps associated with the system and process can be rearranged and/or one or more such steps can be omitted to achieve the same, or similar, results to those described herein.

It is to be understood that the embodiments described hereinabove are cited by way of example, and that the present invention is not limited to what has been particularly shown and described hereinabove.

The invention claimed is:

1. A system for remote Eye Movement Desensitization and Reprocessing (EMDR) therapy comprising:
   a therapist computing platform, comprising a therapist computer screen, a processor and associated memory, wherein the memory includes instructions that the processor executes to perform steps of: establishing a first connection with an EMDR server; communicating, to the EMDR server, parameters controlling a bilateral stimulation (BLS), wherein the parameters include at least one of a start and a duration of the bilateral stimulation; receiving from the EMDR server, by the first connection, an EMDR message indicating a BLS element position, wherein a BLS element position is a screen position of a visual element, or a right or left position of an audio or tactile element; and responsively presenting, on an output device of the therapist computing platform, at least one BLS element at the indicated position;
   a client computing platform, comprising a client computer screen, a processor and associated memory, wherein the memory includes instructions that the processor executes to perform steps of: establishing a second connection with the EMDR server; receiving from the EMDR server, by the second connection, the EMDR message indicating the BLS element position; and responsively presenting, on an output device of the client computing platform, at least one BLS element at the indicated position; and
   the EMDR server, comprising a processor and associated memory, wherein the memory includes instructions that the processor executes to perform steps of: establishing the first and second connections with the respective therapist and client computing platforms; receiving, from the therapist computing platform, the parameters controlling the bilateral stimulation; and broadcasting the EMDR message, simultaneously over the first and second connections, to the respective therapist and client computing platforms, according to the parameters controlling the bilateral stimulation.

2. The system of claim 1, wherein the therapist computing platform is further configured to provide a dashboard for entering the parameters controlling the bilateral stimulation.

3. The system of claim 2, wherein the dashboard further includes options for entering client identifying information.

4. The system of claim 2, wherein the dashboard further includes options for saving client preferences including the parameters for controlling the bilateral stimulation.

5. The system of claim 2, wherein the dashboard further includes options for entering notes regarding a session, wherein the notes may reflect one or more of: a target; an image; positive cognition; negative cognition; Subjective Units of Disturbance (SUD), Validity of Cognition (VOC); client emotions; client body sensations; final SUD; and other remarks.

6. The system of claim 1, wherein the parameters controlling the bilateral stimulation further include a speed of altering a position of the at least one BLS element.

7. The system of claim 1, wherein the parameters controlling the bilateral stimulation further include at least one of a set of visual element features comprising: color, opacity, size, shape, brightness, a movement mode, a height, a direction path, a tracking path, path end points, and a background color, wherein the EMDR message is a first EMDR message, and the EMDR server is further configured to broadcast simultaneously, over the first and second connections to the respective therapist and client computing platforms, a second EMDR message including at least one parameter of the set of visual element features.

8. The system of claim 7, wherein options for the movement mode include a scanning mode and a saccades mode.

9. The system of claim 1, wherein the parameters further include at least one of a set of audio element features comprising volume, a sound effect, and music, wherein the EMDR message is a first EMDR message, and the EMDR server is further configured to broadcast simultaneously, over the first and second connections to the respective therapist and client computing platforms, a second EMDR message including at least one parameter of the set of audio element features.

10. The system of claim 1, wherein the parameters further include a tactile element feature of a vibration intensity of the tactile element, wherein the EMDR message is a first EMDR message, and the EMDR server is further configured to broadcast simultaneously, over the first and second connections to the respective therapist and client computing platforms, a second EMDR message including the tactile element feature.

11. The system of claim 1, wherein the steps performed by the therapist and client computing platforms are further configured to establish a video chat session with the other computing platform.

12. The system of claim 11, wherein the video chat session is a WebRTC video chat, and wherein the EMDR server is configured to provide signaling to establish the WebRTC video chat between the therapist and client computing platforms.

13. The system of claim 1, wherein the therapist computing platform is further configured to display a level of correspondence between the client eye movement and the movement of the visual element on the client screen.

14. The system of claim 1, wherein the EMDR server further configured to automatically modify at least one parameter controlling the BLS according to a level of correspondence between the client eye movement and the movement of the visual element on the client screen.

15. The system of claim 1, wherein the instructions performed by the therapist computing platform and the client computing platform are client-side applications received from the EMDR server by browsers of the respective therapist and client computing platforms.

16. The system of claim 1, wherein the first and second connections between the EMDR server and the respective therapist and client computing platforms are Socket.IO connections.

17. The system of claim 1, wherein the EMDR message indicating a position of a BLS element indicates a position of two or more of the visual, audio, and tactile elements, such that the positions of the multiple BLS elements are synchronized to be on the same side, to the left or right side of the client.

18. The system of claim 1, wherein one of the client computing platform and the therapist computing platform is configured to present the BLS element at a mirrored position of the position of the BLS element presented on the therapist computing platform.

19. The system of claim 1, wherein at least one of the therapist and the client computing platforms are further configured to provide an indicator on their respective computer screens that at least one of the first and second connections with the EMDR server has been established.

20. A computer-based method for remote Eye Movement Desensitization and Reprocessing (EMDR) therapy comprising:

at a therapist computing platform that has a processor and associated memory including instructions for implementing steps of the method, establishing a first connection with an EMDR server; communicating, to the EMDR server, parameters controlling a bilateral stimulation (BLS), wherein the parameters include at least one of a start and a duration of the bilateral stimulation; receiving from the EMDR server, by the first connection, an EMDR message indicating a position of at least one BLS element, wherein the at least one BLS element is at least one of a visual, an audio, and a tactile element, and wherein the indicated position is a screen position of a visual element, or a right or left position of an audio or tactile element; and responsively presenting, on an output device of the therapist computing platform, the at least one BLS element at the indicated position;

at a client computing platform that has a processor and associated memory including instructions for implementing steps of the method, establishing a second connection with the EMDR server; receiving from the EMDR server, by the second connection, the EMDR message indicating the position of the at least one BLS element; and responsively presenting, on an output device of the client computing platform, the at least one BLS element at the indicated position; and at the EMDR server that has a processor and associated memory including instructions for implementing steps of the method, establishing the first and second connections with the respective therapist and client computing platforms; receiving, from the therapist computing platform, the parameters controlling the bilateral stimulation; and broadcasting the EMDR message, simultaneously over the first and second connections, to the respective therapist and client computing platforms, according to the parameters controlling the bilateral stimulation.

* * * * *